(12) United States Patent
Hall et al.

(10) Patent No.: US 9,060,709 B2
(45) Date of Patent: Jun. 23, 2015

(54) METHOD AND APPARATUS FOR QUANTIFYING ORGANIZATION IN COLLAGENOUS TISSUE

(71) Applicant: WISCONSIN ALUMNI RESEARCH FOUNDATION, Madison, WI (US)

(72) Inventors: Timothy Jon Hall, Madison, WI (US); Helen Marcie Feltovich, Park City, UT (US); Lisa McGuire Reusch, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 53 days.

(21) Appl. No.: 13/840,297

(22) Filed: Mar. 15, 2013

(65) Prior Publication Data
US 2014/0276047 A1    Sep. 18, 2014

(51) Int. Cl.
| | | |
|---|---|---|
| A61B 8/00 | (2006.01) | |
| A61B 8/08 | (2006.01) | |
| A61B 8/12 | (2006.01) | |
| A61B 5/00 | (2006.01) | |

(52) U.S. Cl.
CPC ............... *A61B 8/0858* (2013.01); *A61B 8/485* (2013.01); *A61B 8/4494* (2013.01); *A61B 8/12* (2013.01); *A61B 8/5223* (2013.01); *A61B 5/435* (2013.01); *A61B 5/6879* (2013.01)

(58) Field of Classification Search
CPC .... A61B 8/0858; A61B 8/485; A61B 8/4494; A61B 8/12; A61B 8/4223; A61B 5/435; A61B 5/6879
USPC .................................................. 600/437–469
See application file for complete search history.

(56) References Cited

U.S. PATENT DOCUMENTS

| | | | | |
|---|---|---|---|---|
| 5,991,236 | A  * | 11/1999 | Yamamoto ..................... 367/41 |
| 7,061,622 | B2 * | 6/2006 | Rollins et al. ................. 356/497 |
| 7,198,777 | B2 * | 4/2007 | Boppart et al. ................ 424/9.6 |
| 8,194,822 | B2 * | 6/2012 | Rothschild et al. ............. 378/88 |
| 8,480,600 | B2 * | 7/2013 | Friemel et al. .................... 601/2 |
| 8,727,986 | B2 * | 5/2014 | Hall et al. ...................... 600/438 |
| 2006/0121123 | A9 * | 6/2006 | Boppart et al. ............... 424/491 |
| 2010/0106019 | A1 * | 4/2010 | Friemel et al. ................ 600/439 |
| 2010/0222679 | A1 * | 9/2010 | Hall et al. ..................... 600/443 |

* cited by examiner

*Primary Examiner* — Sanjay Cattungal
(74) *Attorney, Agent, or Firm* — Boyle Fredrickson, S.C.

(57) ABSTRACT

An apparatus uses a steered ultrasound beam to assess microstructure of the cervix revealed by backscatter power variation at a range of angles and depth. Analysis of a distribution of power loss at different angles and depths referenced to the structure of the cervix may be used to characterize cervical tissue.

20 Claims, 9 Drawing Sheets

METHOD AND APPARATUS FOR QUANTIFYING ORGANIZATION IN COLLAGENOUS TISSUE

STATEMENT REGARDING FEDERALLY SPONSORED RESEARCH

This invention was made with government support under HD061896 and HD063031 awarded by the National Institutes of Health. The government has certain rights in the invention.

CROSS-REFERENCE TO RELATED APPLICATIONS

--

BACKGROUND OF THE INVENTION

The present invention relates generally to ultrasonic equipment and in particular to an ultrasound machine and method of operating the ultrasound machine to assess the underlying structure of collagen in tissue as may provide insight into cervical competence.

Abnormal cervical behavior contributes to both post-term and preterm pregnancy. With respect to the former, failed inductions of labor cause an increase in cesarean delivery, with longer hospitalizations and greater maternal/neonatal morbidity. Ultrasound prediction (measuring cervical length) and biochemical testing of cervical secretions do not effectively predict which patients at term will have successful inductions.

Preterm delivery is an even greater problem, resulting in significant infant mortality and morbidity (including long-term neurodisability) costing more than $26 billion annually in the US alone. Despite intense research, preterm birth rates have increased over the past century in part due to a lack of effective therapies in the face of a greater number of high-risk pregnancies. Drugs that reduce inflammation and/or inhibit uterine contractions do not prevent preterm birth, nor does cerclage (a suture around the cervix to tie it closed). Currently, ultrasound is used to measure cervical length in an effort to predict preterm delivery (associated with shortening). However, the American College of Obstetricians and Gynecologists cautions that the predictive value of this assessment is of uncertain significance because there are no therapies proven to prevent preterm birth.

The underlying cause of both post-term delivery and preterm delivery appears to be abnormal cervical remodeling (delayed in the first case, premature or accelerated in the second). Cervical remodeling occurs normally during pregnancy and results in a softening of cervical tissue before cervical shortening. The ability to accurately assess and study cervical remodeling (in an effort to understand normal versus abnormal changes) could provide improved prediction of preterm delivery, guide development of innovative therapeutic strategies, and permit monitoring of those pregnancies, as well as predict which patients will have successful inductions of labor.

Cervical shortening in the second trimester is often used to evaluate preterm birth risk because it is inversely related to preterm birth risk regardless of obstetrical history. Nevertheless, most women with a short cervix in the second trimester have successful term deliveries and, further, most nulliparous (first pregnancy) women who deliver preterm have normal second trimester cervical length. This underscores the limitation of this measure.

US Patent Application publication number 2010/0222679, filed Feb. 27, 2009, assigned to the assignee of the present invention and hereby incorporated by reference, describes a technique of assessing the underlying structure of collagen fibers in tissue, for example, in the cervix. This technique looks at normalized ultrasonic backscatter power at different angles in the plane aligned with or crossing the cervical axis. Generally an increase in backscatter loss as a function of angle (compared to the backscatter provided by a phantom with spherical scatters) indicates an increase in organization of that tissue, for example a greater number of aligned collagen fibers.

This analysis of underlying tissue structure (e.g. collagen fiber organization), in addition to or instead of macroscopic tissue properties such as elasticity, presented a new approach and technique for evaluating collagenous tissue such as that of the cervix and thus for the evaluation of cervical competence.

SUMMARY OF THE INVENTION

The present invention advances technique described in the '679 application through an analysis of the pattern of ultrasonic backscatter loss as a function of angle and depth with respect to cervical tissue. Preliminary results suggest that a more sophisticated, and absolute, pattern analysis evaluating measures of symmetry can accurately distinguish between healthy, cervical tissue for non-pregnant women who have given birth and those who have not. This strongly suggests that the technique provides sufficient sensitivity to detect small differences in tissue organization that may provide advanced indication of preterm birth risk.

In one embodiment, the present invention provides a method of assessing tissue structure of the cervix using ultrasound. An ultrasonic beam is applied to tissue at multiple of angles to obtain backscatter power from the tissue at a variety of depths. Variation in this backscatter power both as a function of a tissue angle of the ultrasound beam with respect to a central axis of the cervix and a tissue depth perpendicular to the central axis for a plurality of tissue volume elements is used to determine a distribution of backscatter power loss as a function of tissue angle and tissue depth. This distribution is used to provide a diagnostic indication to an operator.

It is thus a feature of at least one embodiment of the invention to provide a new diagnostic tool for measuring collagenous tissue that looks at multiple dimensions of microscopic tissue organization reflected in backscatter information.

The tissue angle may be at least one of an angle within a plane including the central axis and an angle in a plane perpendicular to the central axis.

It is thus a feature of at least one embodiment of the invention to provide measurements reflecting an assumption of multiple distinct tissue layers in the cervix.

The method may characterize a symmetry of the distribution with respect to tissue angle and the output may be based on this characterization of symmetry.

It is thus a feature of at least one embodiment of the invention to provide a simple measure capturing a tissue organization of collagen fibers perpendicular or tangent to the central axis of the cervix.

The method may characterize a total power loss over multiple voxels of the distribution wherein the output is based on this characterization of total power loss.

It is thus a feature of at least one embodiment of the invention to provide a simple measure capturing tissue organization of collagen fibers aligned in layers.

The method may determine minima in power loss for multiple tissue depths over a range of tissue angles and may characterize a variation in a location of the minima with tissue angle as a function of tissue depth and the output may be based on a variation in location of minima as a function of depth.

It is thus a feature of at least one embodiment of the invention to provide a simple measure capturing uniformity in tissue organization among layers.

The method may further include the step of determining voxels in a range of tissue angles symmetric about the minima and including characterizing the fraction of such voxels in the distribution, and the output may be based on the fraction of such voxels.

It is thus a feature of at least one embodiment of the invention to provide a simple measure indicating general orientation of the fibers with respect to the cervical axis.

The output may be based on a combination of at least two of: a symmetry of the distribution in tissue angle, a sum of backscatter power loss in multiple voxels, a variation in power loss minima as a function of tissue depth and a measure of deviation of the minima from a center tissue angle of the distribution.

It is thus a feature of at least one embodiment of the invention to provide a multifaceted and therefore potentially robust quantitative output useful for clinical evaluations.

The backscatter power loss may be evaluated at a narrow band of frequencies less than half a maximum frequency of the ultrasound beam.

It is thus a feature of at least one embodiment of the invention to provide accurate characterization of microstructure with reduced noise.

The method may further include the step of measuring elasticity of the cervical tissue and the diagnostic indication may be based on a combination of elasticity and the distribution.

It is thus a feature of at least one embodiment of the invention to augment a structure-based analysis of tissue with a measurement of macroscopic tissue properties.

The backscatter power measurement may be any of backscatter power loss, effective scatterer size, integrated backscatter, mean scatterer spacing, and number of scatterers per unit volume.

It is thus a feature of at least one embodiment of the invention to provide a technique adaptable to a wide variety of parametric measuring techniques.

These particular objects and advantages may apply to only some embodiments falling within the claims, and thus do not define the scope of the invention.

DETAILED DESCRIPTION OF THE PREFERRED EMBODIMENT

Figure 1:
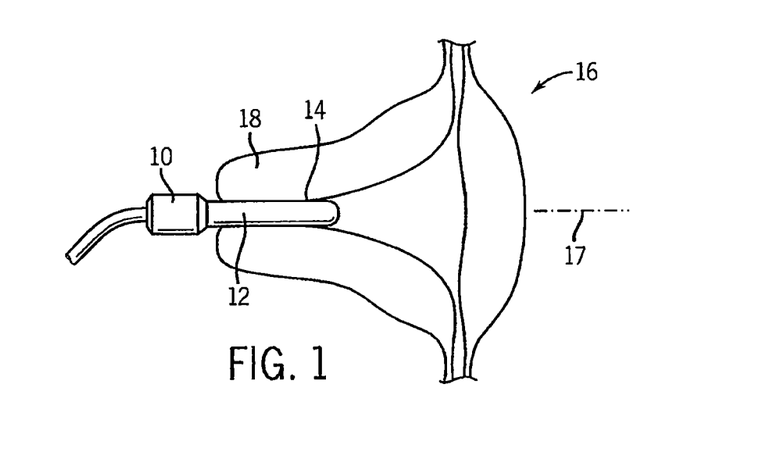
FIG. 1 is a simplified cross-sectional view of the uterus showing the cervical canal and an ultrasonic probe suitable for use with the present invention positioned within the cervical canal.

Referring now to FIG. 1, the present invention provides an ultrasound probe 10 having a generally cylindrical body 12 that may fit within the cervical canal 14 of the uterus 16 to extend along the uterine and cervical axis 17 and to be surrounded by cervical tissue 18. In a preferred embodiment, the cylindrical body 12 has an outside diameter substantially less than 5 mm so as to fit within the cervical canal without substantial dilation of the cervical tissue 18.

Figure 2:
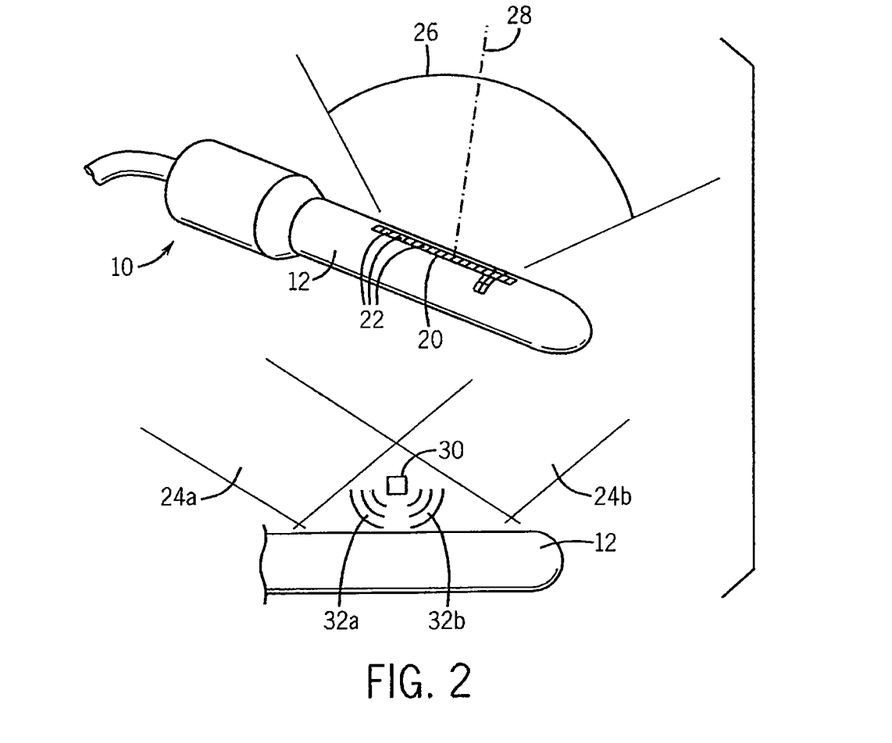
FIG. 2 is a perspective and side elevational view of the probe of FIG. 1 showing axial transducers for steering an ultrasonic beam at a range of axial angles within the cervix.

Referring now to FIG. 2, the outer surface of the cylindrical body 12 provides an axial transducer array 20 extending along the cylindrical body 12 and generally aligned with the axis 17 when the ultrasound probe 10 is within the cervical canal 14. The axial transducer array 20 has a plurality of independently operating transducer elements 22 that may provide for beam steering of a type known in the art. In particular, an ultrasonic beam 24 may be generated and steered over a range of axial angles 26 lying generally within a plane containing the axis 17 and symmetric about a center axis 28 perpendicular to axis 17. In the preferred embodiment, a range of ±20° is obtained. A beam 24a at one angular extreme and 24b at the other angle extreme can alternatively illuminate a voxel 30 of the cervical tissue 18 so that backscatter 32a or 32b at these two angular extremes and a range of angles in between may be collected by the same axial transducer array 20.

Figure 3:
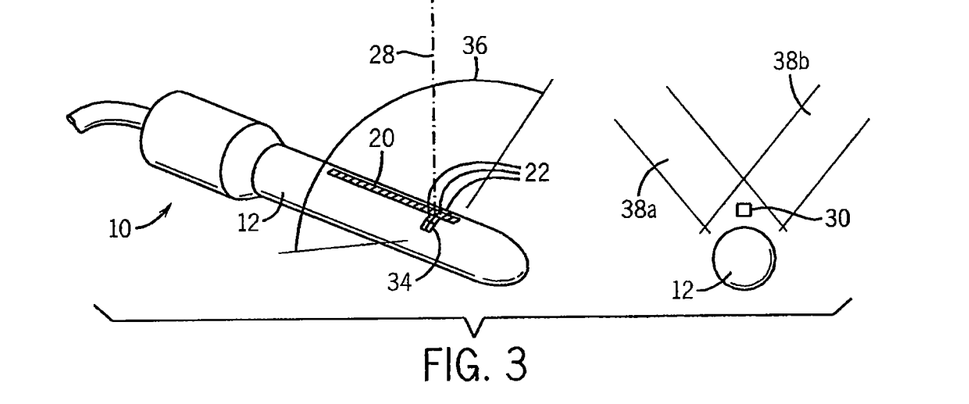
FIG. 3 is a figure similar to that of FIG. 2 providing a perspective and end elevational view of the probe of FIG. 1 showing circumferential transducers for steering an ultrasonic beam at a range of circumferential angles.

Referring to FIG. 3, a circumferential transducer array 34 may optionally be provided crossing the axial transducer array 20 at right angles and arranged around the circumference of the cylindrical body 12 to allow for beam steering of ultrasonic beam 38 within a range of angles 36 in a plane normal to the axis 17 and symmetric about the center axis 28. In this way, the voxel 30 may also be illuminated by beams 38a and 38b over the range of angles 36 and backscatter detected at the cylindrical body 12.

In one embodiment, the transducer array may provide for 7.5 MHz operation with 64 array elements at 100 μm pitch. It will be understood that a two-dimensional transducer array having multiple perpendicular rows and columns can be used instead of the cruciform array described above to provide measurements of the ranges of both angles 26 and 36.

Figure 4:
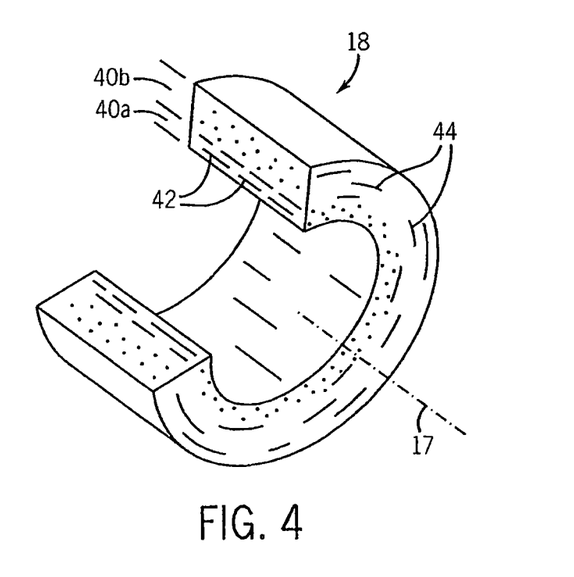
FIG. 4 is an exaggerated fragmentary cross-sectional view of the cervical tissue showing a hypothesized organization of collagen in the cervical tissue early in pregnancy.

Referring now to FIG. 4, while the inventors do not wish to be bound by a particular theory, it is believed that the cervical tissue 18 is comprised of at least two layers of collagen-based tissue including an inner layer 40a and an outer layer 40b. The inner layer 40a may contain collagen fibers 42 arranged parallel to the axis 17 that may be measured by the beams 24 produced by the axial transducer array 20, whereas the outer layer 40b may contain collagen fibers 44 arranged circumferentially about axis 17 to be measured by the beams 38 produced by the circumferential transducer array 34.

Figure 5:
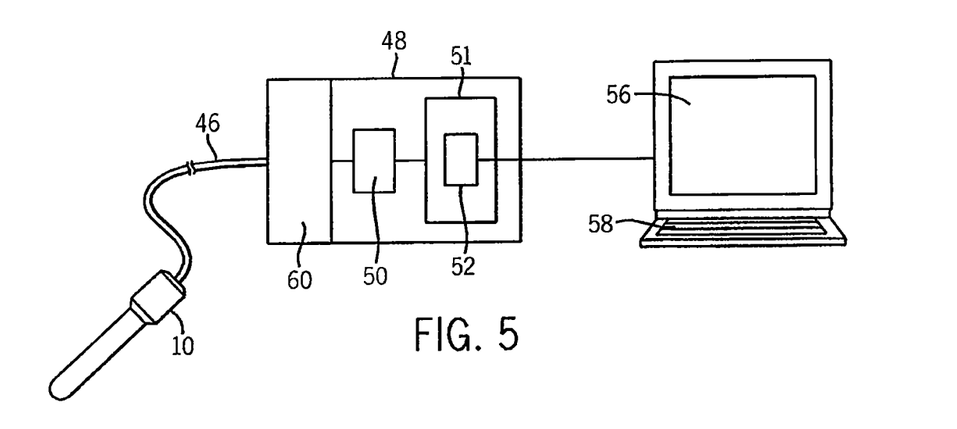
FIG. 5 is a block diagram of an ultrasound machine suitable for use with the probe of FIGS. 1-3 including a processor executing a stored program to process data used in the present invention.

Referring now to FIG. 5, the ultrasound probe 10 may communicate via a flexible cable 46 with an ultrasound machine 48 of the type generally known in the art including, for example, a digital signal processor 60 receiving ultrasonic data and generating ultrasonic output signals, in turn communicating with a standard computer processor 50 executing a program 52 contained in memory 51 to implement the present invention. Generally, the ultrasound machine 48 may also communicate with the display terminal 56 for the outputting of data and a user data entry device 58 such as a keyboard or the like to control operation of the ultrasound machine and to input data according to techniques well known in the art.

Generally phased ultrasonic signals will be created by a digital signal processor 60 under instructions from the processor 50 and transmitted along cable 46 to the transducer arrays of the ultrasound probe 10 to create ultrasonic beams at desired angles and to measure backscatter therefrom. The backscatter signals will be received by ultrasound probe 10 and transmitted through cable 46 to the digital signal processor 60 for analysis by the program 52, the results of which may be displayed on the terminal 56 as will be described.

Figure 6:
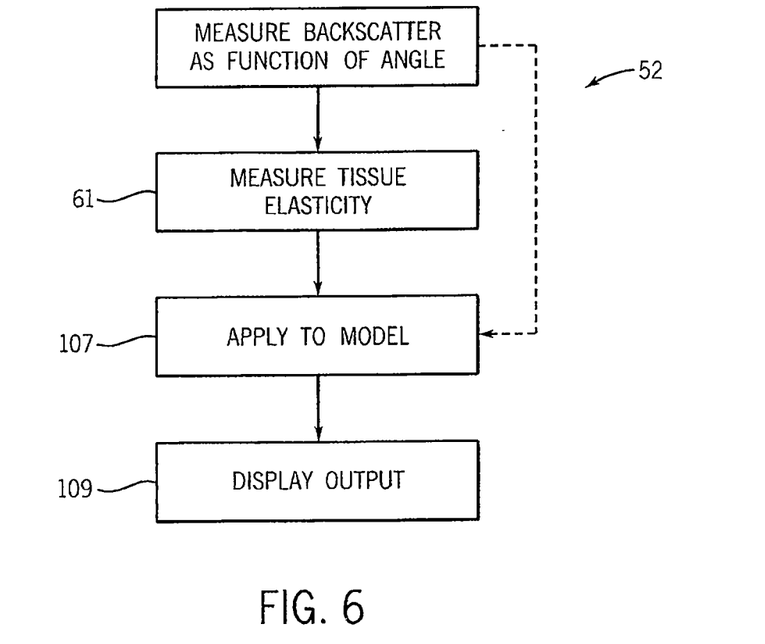
FIG. 6 is a flowchart of the program used in the processor of FIG. 5.

Referring now to FIG. 6, at a first step of the program 52 indicated by process block 62, ultrasonic beams are generated either axially or circumferentially or both, at a range of frequencies, and backscatter acoustic power from those beams is measured by the ultrasound probe 10 for analysis.

Figure 7:
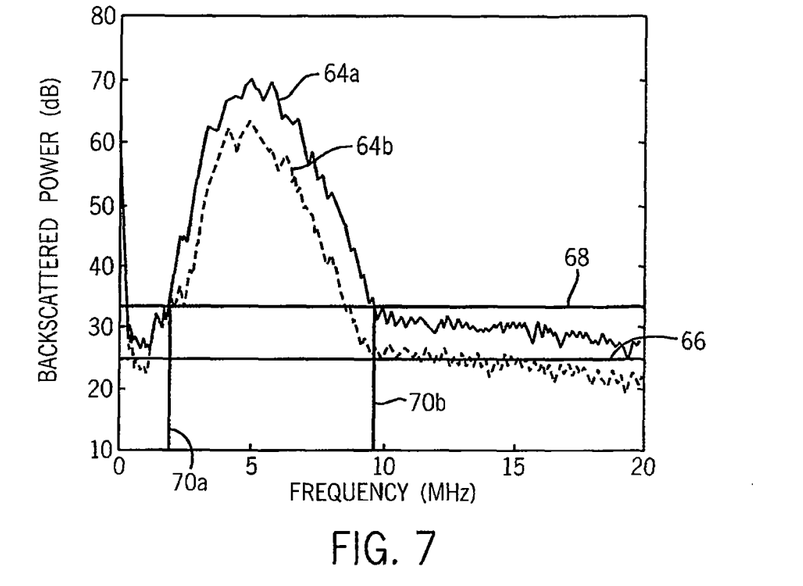
FIG. 7 is a plot of backscatter power spectra at different beam angles showing a decrease in backscatter power at increased angles as a function of frequency.

Referring now to FIG. 7, backscatter information obtained over a range of frequencies at a range of angles provides multiple power spectra 64a and 64b. In this figure, power spectrum 64a is taken normal to the cervical wall along the center axis 28 exhibiting the highest degree of backscatter, and power spectrum 64b is a combination (averaging) of the power spectra obtained at the extreme angles of the beam angulation (i.e. ±20°). Because the tissue structure effects intended to be measured will be symmetric about center axis 28, this averaging process provides for improved signal-to-noise ratio in the measurement while rejecting asymmetrical effects. Multiple additional power spectra may optionally be obtained at different angles.

In one embodiment, the axial transducer array 20 is used to obtain measurements of backscatter at shallow voxel depths corresponding to layer 40a of FIG. 4, and circumferential transducer array 34 is used to obtain power spectra at deeper voxel depths corresponding to layer 40b of the tissue 18.

In a simple embodiment, backscatter at each depth may be characterized by these two power spectra 64a and 64b by establishing a noise floor 66, representing the lowest signal strength of the power spectrum for either of the spectra 64a or 64b and determining a 10 db limit 68 above this noise floor 66 used to define upper and lower frequency limits 70a and 70b of the power spectra 64a and 64b. Between these limits 70a and 70b, the area under each of the spectra 64a and 64b is integrated (for example, from frequencies from 3 to 9 MHz). The resultant backscatter power measurement at the extreme angles (power spectrum 64b) is compared to the backscattered power spectrum 64a at a zero-degree steering angle (perpendicular to the cervical axis 17).

This measured-backscattered power value is then compared to a machine-backscattered power value (not shown) resulting from machine specific features, for example the effective reduction in ultrasound aperture with angle caused by geometrical considerations and a decrease in the sensitivity of the axial transducer array 20 and circumferential transducer array 34 with angle, both of which cause a machine-dependent apparent loss in backscatter power. The machine specific backscattered power value may be determined by the use of a phantom containing spherical isotropic scatterers. This machine-backscattered power value may be computed for each measurement from a stored power spectrum (not shown) using the same integration limits 70a and 70b described above. The measured-backscattered power value is corrected by the machine-backscattered power value to reveal the excess backscattered power loss caused by structure of the cervical tissue 18. This latter excess backscattered power loss value from each of the axial transducer array 20 and circumferential transducer array 34 may be weighted and combined or displayed individually to the user through the graphic terminal 56 or may be further processed as will be described further below.

Figure 8:
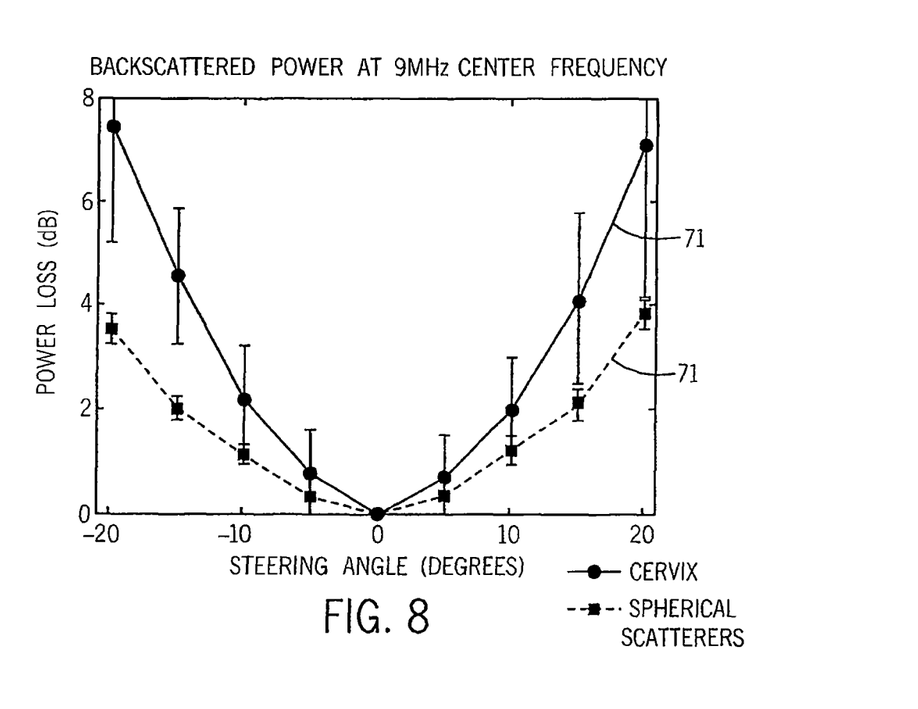
FIG. 8 is a plot of backscatter as a function of angle for center frequencies of 9 MHz for cervical tissue and for a phantom with spherical scatterers.

Referring now to FIG. 8, an alternative measurement of backscatter computes received backscatter power curves 71 as a function of one or more frequencies at multiple angular measurements 72 for both the phantom described above and the cervical tissue 18. A difference in slope of these curves 71 provides the excess-backscattered power loss value (eBSPL) that may be displayed to the user as above.

Referring again to FIG. 7, an alternative measurement parameterizing backscatter, such as the backscatter coefficient, effective scatterer size, integrated backscatter, mean scatterer spacing or number of scatterers per unit volume, could be derived from these angle-dependent power spectra and used to describe the cervical tissue in greater detail.

Alternatively, in any of these cases, the angle related excess-backscattered power loss, or related parameter, as quantified (in one or more dimensions) may be applied to an empirically-derived model that may include additional input parameters entered by the user, for example conception date, cervical length, age of the patient and other data. The model then provides a statistically founded output related to fundamental information desired by the physician, for example risk of preterm delivery, or state of the cervix with respect to a state for successful delivery as will be described below.

In one embodiment the excess-backscattered power loss is combined with elasticity data for the same tissue. The elasticity data augments the backscatter data to better distinguish among microstructure with similar backscattering but different elasticities. While the applicant does not wish to be bound to a particular theory, it is believed that backscatter power loss is increased when the beam encounters anisotropic tissue such as exists in the unripened cervix in comparison to when the beam encounters isotropic tissue in the ripened cervix. This unripened tissue appears to be made up of organized, cylindrical microstructures. At normal incidences (that is, when the cylinder axes of the microstructures are perpendicular to the propagation axis of the ultrasonic wave), a cylinder that is small compared to the acoustic wavelength (as is expected to be the case with collagen structures in the cervix) creates a backscattering that can be explained primarily in terms of resonances related to elastic circumferential waves. However, a wave that encounters a cylinder at a non-normal angle to its axis (either positive or negative angle) excites both longitudinal and circumferential modes of vibration increasing power loss. The extent of the power loss, therefore, can reveal the degree of organization of the tissue.

Backscatter, however, will be similar for long cylindrical fibers that are cross-linked and short cylindrical fibers with no cross-linking. Accordingly, elasticity can be used to resolve these two cases with the longer fibers that produce generally a stiffer and less elastic tissue distinguished by their elasticity from the shorter fibers.

Figure 9:
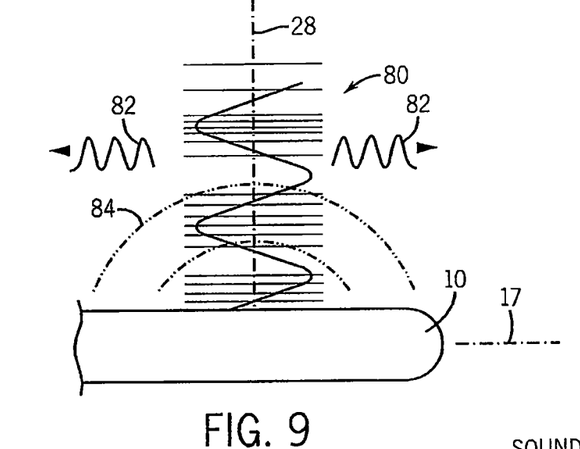
FIG. 9 is a side elevational view of the probe of FIG. 1 in the cervix showing the excitation of shear waves from a "pushing pulse" emitted by the probe in quantitative acoustic radiation force impulse measurements.

Referring now to FIG. 9 and as shown by process block 61 of FIG. 6, the ultrasound probe 10 may be used to measure not only the backscatter as described above, but also the elasticity of the tissue 18 by using the technique of quantitative acoustic radiation force impulse (qARFI). In this technique, a focused compression "push wave" 80 is generated generally along center axis 28 which produces incidental shear waves 82 passing through the tissue 18 generally parallel to the axis 17. B-mode imaging pulses 84 may be used to detect the tissue displacement caused by the shear waves 82 and track a crest of those waves to determine shear wave velocity such as is proportional to Young's modulus, a measure of elasticity. Tools for qARFI and are available from Siemens under the trade name ACUSON S2000 (Virtual Touch Tissue Quantification).

Figure 10:
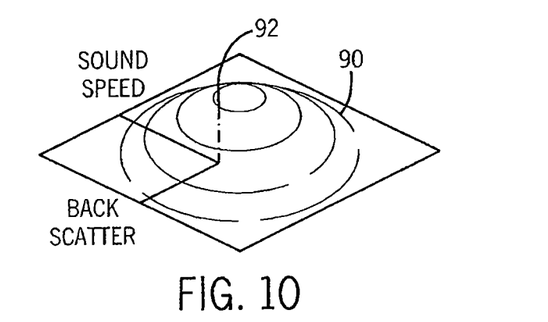
FIG. 10 is a simplified model relating backscatter loss and elasticity to empirically derived preterm risk boundaries.
Figure 11:
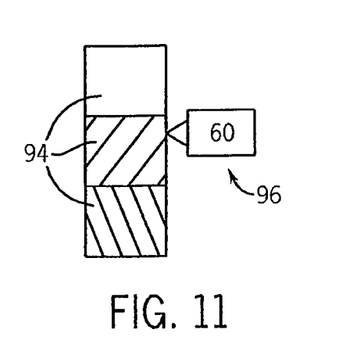
FIG. 11 is an example output displayed for the ultrasound machine of FIG. 5 depicting a risk of preterm delivery in simplified fashion.

Referring to FIG. 10, a model 90 may be generated (in this case depicted as a 3-dimensional surface) that takes backscatter power loss and shear wave sound speed as inputs to provide an output point 92 on a model surface empirically linked to risk of preterm delivery. As indicated by FIG. 11, this output point 92 may be mapped to a simple scale 94 depicting risk of preterm delivery relative to broad categories, for example high-risk, medium risk, and low risk, and/or a numeric output 96 may be provided providing the same information, for example, as a percentage. The model may incorporate additional input dimensions as described above, such as gender, conception date, and the like, such multidimensional models providing a multidimensional surface not readily depicted.

Figure 12:
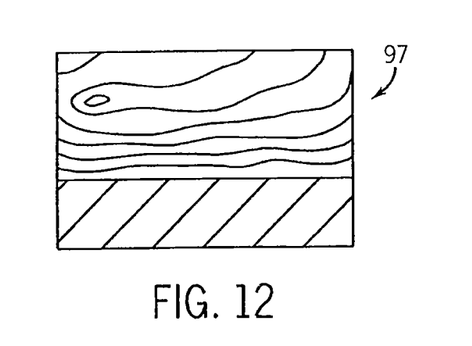
FIG. 12 is a graphical display of a backscatter power image for investigational study.

Referring to FIG. 12, elasticity data and backscatter data may also be displayed as an image 97 in the manner of a conventional B-mode image or superimposed on a B-mode image to characterize different portions of the cervical tissue in the image. In this way, the phenomenon of graduated ripening of the cervix from the proximal to distal portions may be studied.

Figure 13:
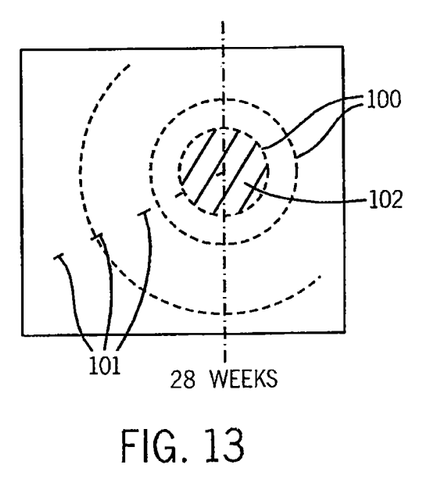
FIG. 13 is a graphical display representing a model of backscatter measurements during a normal pregnancy superimposed on measurements from a particular patient used for predicting due date or making decisions about delivery.
Figure 14:
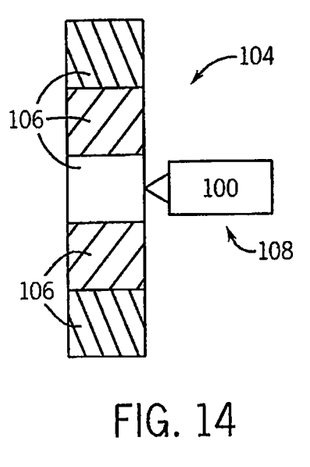
FIG. 14 is a figure similar to that of FIG. 11 showing a simplified display indicating concurrence between a given pregnancy and a statistically normal pregnancy.

Referring now to FIG. 13 and as shown by process block 107 of FIG. 6, it will be understood that the measured data of backscatter and/or shear wave speed may also be used to evaluate the course of pregnancy, for example, by the generation of boundaries 100 indicating the state 102 of remodeling of the cervix, for example, at the time of a standard vaginal delivery in a sampled population together with data from an individual patient, assisting the physician in assessing a due date and/or appropriate time for induced labor for delivery. Again, as shown in FIG. 14 and process block 109 of FIG. 6, the data of the model of FIG. 13 may be extracted to a simple display 104 having zones 106 showing degrees of remodeling of the cervix for delivery and providing a quantitative output 108 for the physician.

Figure 15:
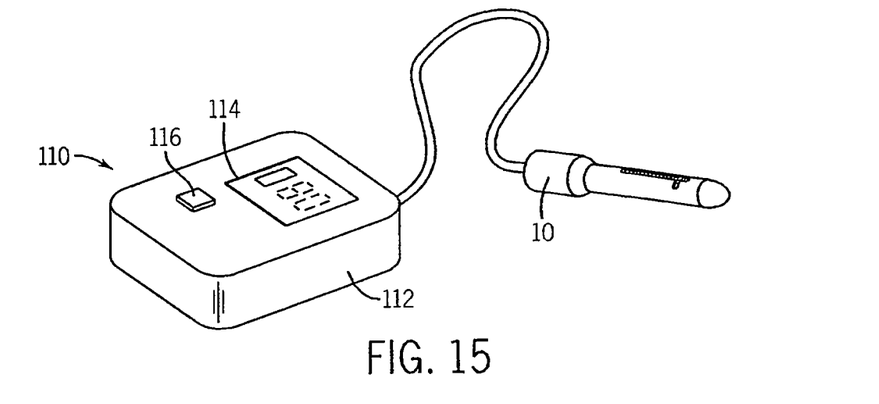
FIG. 15 is a perspective representation of a handheld device for implementing the present invention.

Referring to FIG. 15, although the present invention may be incorporated into a standard imaging ultrasound machine providing B-mode imaging capabilities, the present invention may also be provided in a portable stand-alone instrument 110 in which the ultrasound probe 10 may connect to a hand-held unit 112 providing a simple graphic display 114 and as little as a single activation button 116, and preprogrammed to make the measurements of the present invention.

MULTILAYER ANALYSIS

Referring now to FIGS. 16a and 16b, the ultrasound probe 10 described above may be positioned to obtain backscatter power loss measurements at multiple voxels 120 within the tissue 18 over a range of angles 26 generally within a plane 122, including axis 17 at a variety of depths 124 perpendicular to axis 17 for each of those angles. Importantly, a tissue angle 36 and tissue depth 124 is preserved for each power loss measurement of each voxel 120 indicating an angle and depth respect to the structure of the cervix. In this case, the structure may be a central axis of the cervical canal coincident with axis 17 along which the cylindrical body 12 ultrasound probe 10 (shown in FIG. 1) will naturally lie.

These multidimensional measurements may be made for "well-organized" tissue 18 as shown in FIG. 16a, in which collagen fibers 44 extend generally parallel to the axis 17 and for "unorganized" tissue 18' shown in FIG. 16b for which collagen fibers 44 vary in alignment with axis 17.

Figure 16:
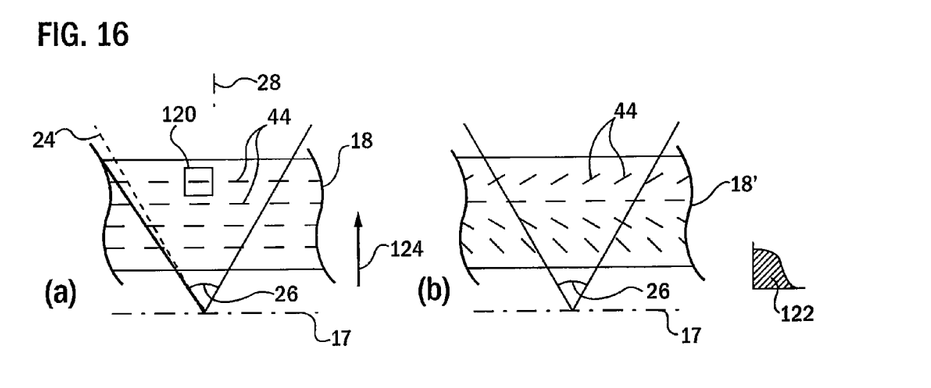
FIGS. 16a and 16b are simplified elevational cross-sections through the cervix wall showing acquisition of data over multiple angles and depths with respect to the cervix wall for well-organized and unordered tissue.
Figure 17:
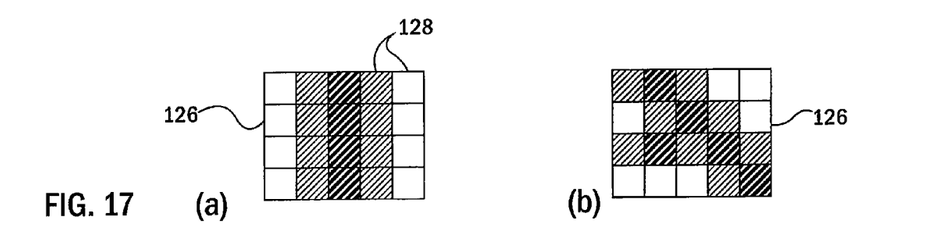
FIGS. 17a and 17b are simplified schematic representations of data distributions for the well-organized and unordered tissue of FIG. 16.

The measurements for each of the voxels 120 may be assembled into distributions including distribution 126 of FIG. 17a for the tissue of FIG. 16a and the distribution 126' of FIG. 17b for the tissue of FIG. 16b. Each distribution 126 or 126' provides a rectilinear matrix of data elements 128 associated with different corresponding voxels 120, each data element 128 holding a quantitative excess backscatter power loss (eBSPL) value. In the distributions 126 or 126', the data elements 128 for each column correspond to a common tissue angle 36 along which the voxels 120 corresponding to the elements 128 of that column lie. In this way the tissue angle, being referenced with respect to a predetermined cervical structure, is preserved for each data element 128. Likewise, the data elements 128 for each row correspond to a common tissue depth 124 at which the voxels 120 corresponding to the element 128 of that row lie. Again, tissue depth, being referenced with respect to cervical structure, is preserved in the distributions 126 and 126' by virtue of this organization.

The distributions 126 and 126' may, for example, encompass a range of depth of 5 to 11 millimeters into the cervical tissue measured perpendicular to axis 17 and a range of angles of −40 to +40 degrees with respect to a normal to axis 17. Data from a steered ultrasound beam 24 may be interpolated to constant depths, that is, consistent with the steering angle at zero degrees.

In the simplified representations of the distributions 126 and 126' of FIG. 16, darker shaded elements 128 generally represent less eBSPL. It may be understood generally from these diagrams that for the well-organized tissue of FIG. 16a, those voxels 120 associated with measurement by an ultrasound beam 24 having greater tissue angle (that is at a greater angle from a normal to axis 17) will present collagen fibers 44 that are decreasingly perpendicular to the ultrasound beam 24 making the measurement. For this reason, a greater eBSPL will occur away from a perpendicular to axis 17 within the measurement plane 122 and this increase in eBSPL will be largely symmetric within the distribution 126, 126' for each tissue depth.

In contrast, for the unorganized fibers 44 of tissue 18' of FIG. 16b, the distribution 126' will exhibit far less symmetry in the increase in eBSPL with greater tissue angle. More generally, the present inventors have determined that the pattern of eBSPL in the distribution 126, 126' may provide substantial insight into otherwise hidden structure of the cervical tissue.

Figure 20:
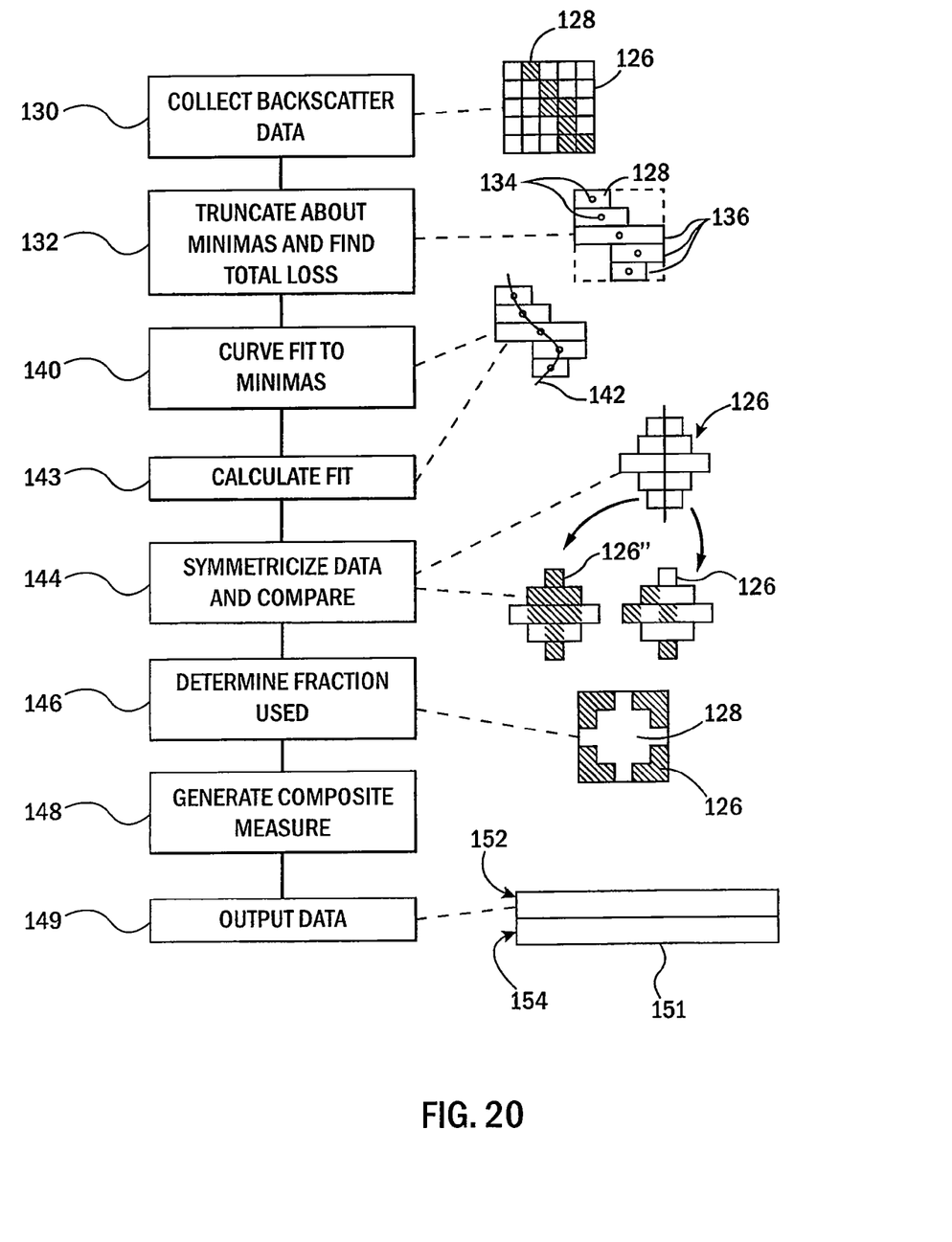
FIG. 20 is a flowchart and simplified data diagram illustrating the steps of the flowchart.

Referring now to FIG. 20, a first step of this process, as may be implemented by program 52, is a collection of backscatter measurement producing values of eBSPL at multiple data elements 128 obtained as indicated by process block 132 to produce a distribution 126.

At process block 132, power loss minima 134 may be identified for each depth in the distribution 126 and data elements 128' outside of a symmetrical range 136 about each minimum 134 may be truncated.

Figure 18:
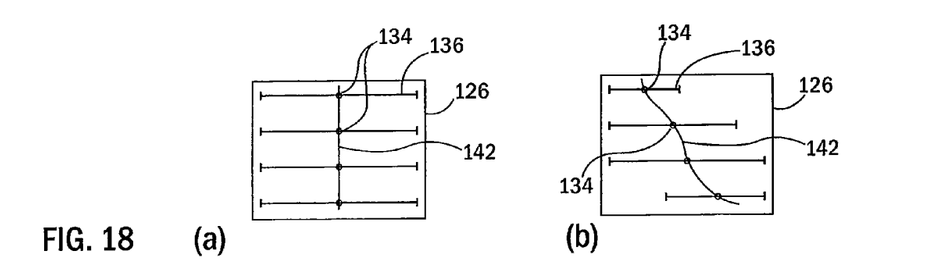
FIGS. 18a and 18b are phantom representations of the data distributions of FIG. 17 showing processing of that data for the evaluation of symmetry and other measures.

Referring also to FIG. 18a, for well-organized tissue, such as is depicted in FIG. 16a and with an ultrasound probe aligned with axis 17, the minima 134 will be approximately along a center-most vertical column through the distribution 126. In this case, the symmetrical ranges 136 for each row will extend substantially the entire angular range or width of the distribution 126. In contrast, for the unordered tissue depicted in FIG. 16b, minimas 134 shown in FIG. 18b may be displaced toward one side or the other of the distribution 126 resulting in symmetrical ranges 136 that are less than the full width of the distribution 126. The truncation process marks those data elements 128 outside of the symmetrical range 136 to be ignored in the processing.

Once this truncation is complete, a total strength of scattering power loss L may be determined by summing the un-truncated data of data elements 128 over the entire distribution 126 normalized by the number of depth levels according to the equation:

$$L = \frac{\sum_{angles}\sum_{depths} P(\text{angles, depths})}{N} \quad (1)$$

where L is the strength of loss, P (angles, depths) is the excess backscattered power loss eBSPL (being the difference between the backscatter power for the tissue and for the phantom as calibrated to the probe) associated with each data element 128 indexed by tissue angle and tissue depth, and N is the total number of different tissue depth levels being analyzed. Generally, a greater total power loss L will be associated with well-ordered tissue.

At process block 148, curve 142 may be fit to the minima 134 using a polynomial, for example a third order polynomial. The limited order of this polynomial curve 142 imposes limitations on angle variations as a function of depth in the fit to the minimas 134, a type of limitation that would be expected for well-organized tissue. Accordingly, the "goodness of fit" between the curve 142 and the minima provides a measurement of how well-organized the tissue is. In this regard, at process block 143, a goodness of fit value $\lambda^2$ may be obtained according to standard statistical techniques. This goodness of fit $\lambda^2$ relates the actual locations of the minima 134 to the corresponding values of polynomial curve 142. Other measurements of goodness of fit are also contemplated. Generally, well-ordered tissue is associated with a better goodness of fit $\lambda^2$.

Figure 19:
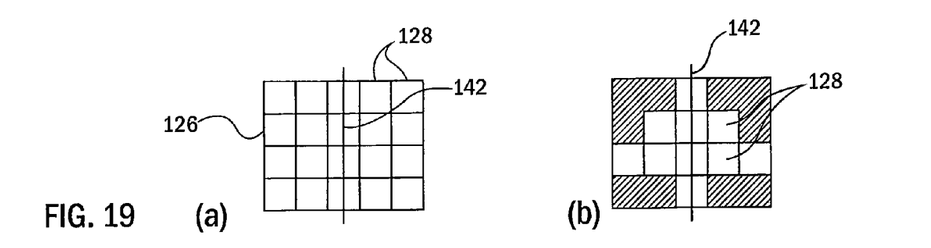
FIGS. 19a and 19b are figures similar to those of FIG. 18 showing a truncation process used in one embodiment of the invention.

Referring now to process block 144 and FIGS. 19a and 19b, the untruncated data elements 128 of the distribution 126 may then be made symmetrical by sliding each row of the distribution 126 so that the curve 142 becomes straight, vertical and bisects the remaining data elements 128 that were not truncated. As shown generally in FIG. 19a, the well-organized data corresponding to tissue of FIG. 16a may result in very little truncation and very little realignment leaving all of the data elements 128 of the distribution 126 substantially as acquired. In contrast, the unordered data of FIG. 19b corresponding to the tissue of FIG. 16b may experience substantial shifting of the data elements 128 along each row to effect this alignment.

The aligned data elements 128 may then have their data transformed to extract a symmetrical component of that data. This may be done by computing a discrete cosine transform across each data element 128 of each row, discarding the odd ordered terms of the transform (setting them to zero) and then computing the inverse discrete cosine transform and applying those values back into the data elements 128. This data forms a symmetricized data distribution 126'. A data element-by-data element comparison between the original truncated and aligned data distribution 126 and the symmetricized data distribution 126' is then performed to produce a measure of asymmetry according to the formula:

$$A = \sqrt{\frac{\sum_{angles}\sum_{depths}(P_{aligned}(\text{angles, depths}) - P_{symm}(\text{angles, depths}))^2}{\sum_{angles}\sum_{depths}(P_{aligned}(\text{angles, depths}))^2}} \quad (2)$$

where $P_{aligned}$ is the data distribution 126 after process block 143 and $P_{symm}$ is the data distribution 126" after process block 144. Generally, well-organized tissue leads to a smaller value of A representing a smaller difference between these two arrays 126 and 126".

At process block 146, the fraction of un-truncated data elements 128 out of the original data elements of the distribution 126 may be determined as $f_{used}$. This basically is a measure of how far the minimas 134 are from the center of the data distribution 126. Generally the more well-ordered the tissue, the larger this fraction.

Each of these individual measures may be individually displayed to the user. Alternatively or in addition, as indicated by process block 148, each of these measures may be combined in a total value O according to the formula:

$$O = \frac{L * f_{used}}{\lambda^2 * A} \quad (3)$$

using the above defined terms.

As shown in process block 149, the results of these measurements may be output, for example, in a table 151 providing in one row, normal values 152, for example, representing cervical tissue having a structure expected for a first birth going to full term, and in one row 154 measurements for the given patient, in this case showing cervical tissue having a structure likely to lead to preterm delivery for a first birth. An example of the data table is provided below in Example I.

Figure 21:
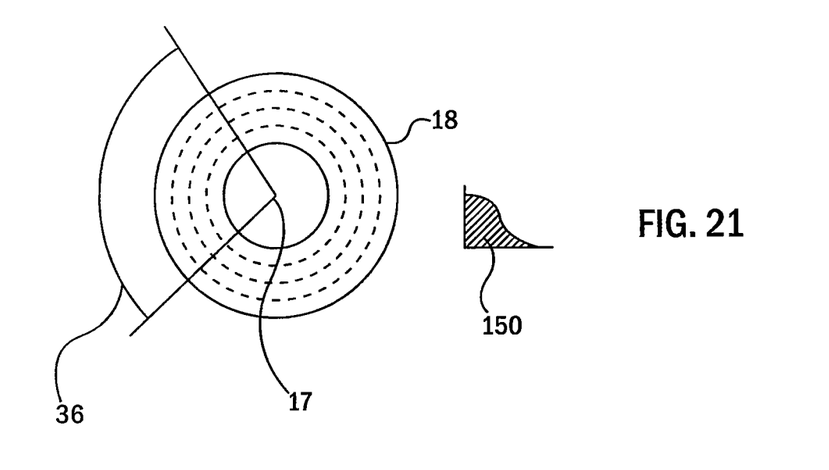
FIG. 21 is a figure similar to that of FIG. 16 but taken in a perpendicular plane showing well-organized tissue.

Referring now to FIG. 21, it will be appreciated that the same analysis described above with respect to FIGS. 16a and 16b can be conducted about axis 17 using a range of angles 36 lying within a plane 150 perpendicular to axis 17 and a depth representing a radius line away from axis 17. In both of the above cases, depth reflects an assumption of homogeneity in the tissue at constant depth.

EXAMPLE I

Normal healthy cervical tissue was obtained from volunteers undergoing hysterectomy for reasons that did not involve the cervix. Twenty-seven samples were obtained from women who had given birth (multiparous) of which 10 had ripened cervices, ripening referring to a process where the cervix softens to become more distensible in preparation for dilation, labor and delivery.

Samples were measured using the above techniques within one hour of removal employing a Siemens Acuson S2000 ultrasound machine with a commercially available AcuNav 1° F. IntraCardiac probe with a diameter of three millimeters. The element size and spacing for this probe is consistent with a phased array probe allowing electronic steering of a phased array ultrasound beam through large angles without encountering grating lobes. With the transducer inside the canal of the cervix, radiofrequency ultrasound echo data with a center frequency of 7.27 megahertz was collected from linear phased beams that were electronically steered between plus and minus 40 degrees in increments of four degrees. Initially the transducer was placed just shy of the internal os of the cervix. The transducer was then translated along the length of the cervix such that angle dependent RF data was collected for the whole length of the cervix. This was done for both anterior and posterior quadrants of the cervix. The same beam steering experiment was performed in an ultrasound phantom containing spherical scatters to account for losses in the transducer's effective aperture and sensitivity as the beam was steered.

For each steering angle, the ultrasound data from both the cervical samples and the reference phantom was broken up into four-millimeter axial windows with 90 percent overlap between windows. A standard Hann window was then applied and the power spectrum calculated from the windowed RF signal via Fourier transform. Backscatter power for each angle was obtained by integrating the power spectrum between high and low cutoff frequencies. The frequency limits for integration were chosen such that the signal was at least 10 decibels above the noise floor. The frequency limits were chosen using the smallest frequency range in an angle-dependent data set so that the same frequency range could be used for all angles of windows in a single set.

The results of the above-described measurements with respect to two actual samples representing a highly ordered and highly disordered sample are provided below:

TABLE 1

| Sample | Strength of loss | Asymmetry | $X^2$ | Fraction used | Order parameter |
|---|---|---|---|---|---|
| Well-organized | 110 | 0.123 | 3.43 | 0.946 | 247 |
| Disordered | 39.4 | 0.321 | 274 | 0.660 | 0.297 |

The value of the order parameter is highly normormal which may be remedied somewhat by taking the logarithm of the order parameter or its constituent values.

It is specifically intended that the present invention not be limited to the embodiments and illustrations contained herein, but include modified forms of those embodiments including portions of the embodiments and combinations of elements of different embodiments as come within the scope of the following claims. For example, the invention does not require a cervical probe but conceivably could be done transabdominally.

While the above description uses the example of an ultrasound probe inserted in the cervical canal, it will be appreciated that data in the necessary orientation may be obtained with other probe locations, for example, a probe applied to an outer surface of the cervix.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to a computer can be understood to include one or more processors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A method of assessing tissue structure of a cervix using ultrasound comprising the steps of:
   (a) applying an ultrasonic beam to tissue at multiple of angles to obtain backscatter power measurements from the tissue at a variety of depths so that tissue at each depth is measured at a variety of angles and recording a tissue angle measurement of the ultrasound beam with respect to a central axis of the cervix and a tissue depth measurement perpendicular to the central axis for each of the backscatter power measurements at the variety of depths and angles;
   (b) quantify a variation in backscatter power measurements both as a function of tissue angle and tissue depth for a plurality of tissue volume elements;
   (c) process the variation in backscatter power both as a function of tissue angle and tissue depth to determine a distribution among the volume elements of backscatter power loss as a function of tissue angle and tissue depth; and
   (d) output a diagnostic indication to an operator based on the distribution.

2. The method of claim 1 wherein the tissue angle is at least one of an angle within a plane including the central axis and an angle in a plane perpendicular to the central axis.

3. The method of claim 1 further including characterizing a symmetry of the distribution with respect to tissue angle and wherein the output is based on this characterization of symmetry.

4. The method of claim 1 further including characterizing a total power loss over multiple voxels of the distribution and wherein the output is based on this characterization of total power loss.

5. The method of claim 1 further including determining minima in power loss for multiple tissue depths over a range of tissue angles and characterizing a variation in a location of the minima with tissue angle as a function of tissue depth and wherein the output is based on a variation in location of minima as a function of depth.

6. The method of claim 1 further including the step of determining voxels in a range of tissue angles symmetric about minima in the range and including characterizing a fraction of such voxels in the distribution and wherein the output is based on the fraction of such voxels.

7. The method of claim 1 wherein the output is based on a combination of at least two of a symmetry of the distribution in tissue angle, a sum of backscatter power loss in multiple voxels, a variation in power loss minima as a function of tissue depth and a measure of deviation of the minima from a center tissue angle of the distribution.

8. The method of claim 1 wherein the backscatter power loss is evaluated at a narrow band of frequencies that are less than a range of frequencies defined by half a maximum frequency of the ultrasound beam.

9. The method of claim 1 further including the step of measuring elasticity of tissue of the cervix and wherein the diagnostic indication is based on a combination of elasticity and the distribution.

10. The method of claim 1 wherein backscatter power measurement is selected from the group consisting of backscatter power loss, effective scatterer size, integrated backscatter, mean scatterer spacing, and number of scatterers per unit volume.

11. An apparatus for assessing tissue structure of a cervix using ultrasound comprising:
   an ultrasound transducer and circuit adapted to apply an ultrasonic beam to tissue at multiple of angles to obtain backscatter power measurement from the tissue at a variety of depths so that tissue at each depth is measured at a variety of angles;
   an electronic computer executing a program stored in non-transient media to:
   (a) receive backscatter power measurements from the cervix at a variety of depths and variety of angles for each depth;
   (b) recording a tissue agile measurement of the ultrasound beam with respect to a central axis of the cervix and a tissue depth measurement perpendicular to the central axis for each of the backscatter power measurements at the variety of depths and angles;
   (c) quantify a variation in backscatter power measurements both as a function of tissue angle and tissue depth for a plurality of tissue volume elements;
   (d) process the backscatter power both as a function of tissue angle and tissue depth to determine a distribution among the volume elements of backscatter power loss as a function of tissue angle and tissue depth; and
   (e) output a diagnostic indication to an operator based on the distribution.

12. The apparatus of claim 11 wherein the tissue angle is at least one of an angle within a plane including the central axis and an angle in a plane perpendicular to the central axis.

13. The apparatus of claim 11 wherein the electronic computer further executes the program to characterize a symmetry of the distribution with respect to the tissue angle and wherein the output is based on this characterization of symmetry.

14. The apparatus of claim 11 further including characterizing a total power loss over multiple voxels of the distribution and wherein the output is based on this characterization of total power loss.

15. The apparatus of claim 11 further including determining minima in power loss for multiple depths over a range of tissue angles and characterizing a variation in a location of the minima with tissue angle as a function of tissue depth and wherein in the output is based on a variation in location of minima as a function of tissue depth.

16. The apparatus of claim 11 further including the step of determining voxels in a range of angles symmetric about minima and including characterizing a fraction of such voxels in the distribution and wherein the output is based on the fraction of such voxels.

17. The apparatus of claim 11 wherein the output is based on a combination of at least two of a symmetry of the distribution in tissue angle, a sum of backscatter power loss in multiple voxels, a variation in power loss minima as a function of tissue depth and a measure of deviation of the minima from a center tissue angle of the distribution.

18. The apparatus of claim 11 wherein the backscatter power loss is evaluated at a narrow band of frequencies less than half a maximum frequency of the ultrasound beam.

19. The apparatus of claim 11 wherein the electronic computer further executes the program to measure elasticity of the tissue of the cervix and wherein the diagnostic indication is based on a combination of elasticity and the distribution.

20. The apparatus of claim 11 wherein backscatter measurement is selected from the group consisting of backscatter power loss, effective scatterer size, integrated backscatter, mean scatterer spacing, and number of scatterers per unit volume.

\* \* \* \* \*